United States Patent [19]
Olivo et al.

[11] Patent Number: 5,851,757
[45] Date of Patent: *Dec. 22, 1998

[54] INDICATOR CELL LINE FOR DETECTING RNA VIRUSES AND METHOD THEREFOR

[75] Inventors: Paul D. Olivo; Sondra Schlesinger, both of St. Louis, Mo.

[73] Assignee: Washington University, St. Louis, Mo.

[*] Notice: The term of this patent shall not extend beyond the expiration date of Pat. No. 5,591,579.

[21] Appl. No.: 774,406

[22] Filed: Dec. 31, 1996

Related U.S. Application Data

[63] Continuation of Ser. No. 171,214, Dec. 21, 1993, Pat. No. 5,591,579.

[51] Int. Cl.$^6$ .............................. C12N 5/10; C12Q 1/02; C12Q 1/04; C12Q 1/70
[52] U.S. Cl. ................................ 435/4; 435/5; 435/325; 435/975
[58] Field of Search ................................ 435/5, 4, 325, 435/975

[56] References Cited

U.S. PATENT DOCUMENTS

| | | | |
|---|---|---|---|
| 4,708,818 | 11/1987 | Montagnier et al. | 435/5 |
| 4,719,177 | 1/1988 | Baltimore et al. | 435/91.51 |
| 4,798,797 | 1/1989 | Montagnier et al. | 435/235.1 |
| 5,217,879 | 6/1993 | Huang et al. | 435/69.1 |

FOREIGN PATENT DOCUMENTS

| | | |
|---|---|---|
| 0463570 A1 | 1/1992 | European Pat. Off. . |
| WO89/08145 | 9/1989 | WIPO . |

OTHER PUBLICATIONS

Kimpton, J., et al., Detection of Replication–Competent and Pseudotyped Human Immunodeficiency Virus with a Sensitive Cell Line on the Basis of Activation of an Integrated β–Galactosidase Gene, *J. Virol.* 66:2232–2239 (1992).

Levis, R., et al., Deletion Mapping of Sindbis Virus DI RNAs Derived from cDNAS Defines the Sequences Essential for Replication and Packaging, *Cell* 44:137–145 (1986).

Rice, C., et al., Production of Infectious RNA Transcripts from Sindbis Virus cDNA Clones: Mapping of Lethal Mutations, Rescue of a temperature–Sensitive marker and In Vitro Mutagenesis To Generate Defined Mutants, *J. Virol.* 61–3809–3819 (1987).

Ramaswamy, R., et al., Analysis of Sindbis Virus Promoter Recognition In Vivo, Using Novel vectors with Two Sub-genomic mRNA Promotors, *J. Virol.* 65:2501 (1991).

Hertz, J., et al., Utilization of Heterologous Alphavirus Junction Sequences as Promoters by Sindbis virus, *J. Virol.* 66:857–864.

Liljestrom, P., et al., A New Generation of Animal cell Expression Vectors Based on the Semliki Forest Virus Replicon, *Bio/Technology* 9:1356 (1991).

Enami, M., et al., High–Efficiency formation of Influenza Virus Transfectants, *J. Virol.* 65:2711–2713 (1991).

Luytjes, W., et al., Amplification Expression and Packaging of a Foreign Gene by Influenza Virus, *Cell* 59:1107–1113 (1989).

Enami, M., et al., Introduction of site–specific mutations into the genome of influenza virus, *Proc. Natl. Acad. Sci.* 87:3802–3805 (1990).

Park, K., et al., Rescue of a foreign gene of Sendai virus, *Resc. Natl. Acad. Sci.* 88:5537–5541 (1991).

Collins, P., et al., Rescue of synthetic analogs of respiratory syncytial virus genomic RNA and effect of truncations and mutations on the expression of a foreign reporter gene, *Proc. Natl. Acad. Sci.* 88:9663–9667 (1991).

Xiong, C., et al., Sindbis Virus: An Efficient, Broad Host Range Vector for Gene Expression in Animal Cells, *Science* 243:1188–1191.

Rocancourt et al., Journal of Virology 64(6):2660–2668 (1990).

Levis et al., Proc. Natl. Acad. Sci. USA 84:4811–4815 (1987).

*Primary Examiner*—Johnny F. Railey, II
*Attorney, Agent, or Firm*—Howell & Haferkamp, L.C.

[57] ABSTRACT

Cell lines and methods are disclosed for detecting the presence of RNA viruses in a specimen. The cell lines are stably transformed with a DNA molecule that includes a promoter capable of being recognized by the DNA dependent RNA polymerase of the cell capable of directing the transcription of a cDNA of a structurally defective RNA virus genome operably coupled to the promoter. The cDNA contains a structural coding sequence encoding a selected reporter gene product. The RNA molecules transcribed by the DNA dependent RNA polymerase are not capable of causing the translation of the reporter gene in the cell except when an active related virus that provides the necessary trans-acting enzymes to cause the increased replication of the RNA containing the reporter gene which is then translated into the reporter gene product is provided. Methods utilizing the cell lines of this invention to detect RNA viruses in a specimen by incubating the specimen with the cell line and assaying for expression of the reporter gene and a kit containing a supply of the cells and a supply of the reagents necessary for the detection of the reporter gene product are also provided.

14 Claims, 5 Drawing Sheets

INDICATOR CELL LINE FOR DETECTING RNA VIRUSES AND METHOD THEREFOR

This is a continuation of application Ser. No. 08/171,214 filed on Dec. 21, 1993 now U.S. Pat. No. 5,591,579.

This invention was made with Government support under Grant No. AI 11377 awarded by the National Institutes of Health. The. Government has certain rights in the invention.

BACKGROUND OF THE INVENTION

(1) Field of the Invention

This invention generally relates to virology, and more particularly to the provision of a mammalian cell line that has been genetically engineered to permit the detection and quantitation of the presence of an RNA virus in a biological specimen and a method for detecting RNA viruses using these cells.

(2) Description of Related Art

The methods by which biologically active or infectious viruses are detected at the clinical level have changed little over recent decades. The standard diagnostic assay for viral infections involves inoculation of specimens onto tissue culture cells followed by detection of infectious virus by microscopic observation of a characteristic cytopathic effect. This method has been supplemented by automated methods that detect viral antigen or viral nucleic acid, but an automated method for the detection of infectious virus is not presently available. The automated assays that detect viral antigen often provide the advantages of rapidity and specificity, but they also often lack the requisite sensitivity necessary for a clinically reliable assay. Automated assays that detect the presence of viral nucleic acid have also recently been developed, but such assays detect viral nucleic acid and not infectious virus. The detection of infectious virus is often preferred because it definitively indicates the existence of an ongoing viral infection with active viral replication. Moreover, assays detecting only viral nucleic acid may only be indicative of the presence of a remnant of a past infection or the presence of a latent infection and the treatment necessary for an ongoing infection may be different than that for a latent or past infection. Thus, the provision of a rapid, specific, sensitive and cost-efficient assay for the detection of infectious virus would be a valuable addition to a clinical diagnostic laboratory and to research laboratories needing a rapid and sensitive assay to determine the presence or absence of an RNA virus in a fluid.

Recently, methods for detecting infectious DNA viruses and RNA viruses that replicate through a DNA intermediate, such as HSV and HIV, have been disclosed that utilize a genetically engineered cell line containing a chimeric gene having a reporter gene under the control of a regulatory region that is activated in the presence of active virus to cause expression of the reporter gene product. Rocancourt, et al. J. Virol. (1990) 64:2660–2668; Kimpton, J. and Emerman, M., J. Virol. (1992) 66:4:2232–2239. This approach has proved useful for the detection of DNA viruses and RNA viruses that replicate through DNA, but is not applicable to the detection of RNA viruses that replicate through an RNA intermediate and not through DNA. A primary reason for this is that RNA viruses replicate in the cytoplasm and have no known mechanism which would permit the RNA virus to transactivate a DNA promoter contained within the nucleus of a cell.

Numerous RNA viruses are pathogenic to humans and their diagnosis is important clinically and for various research purposes. The Togavirus family of RNA viruses includes the genus Alphavirus which includes many important viral species such as Sindbis virus, Semliki Forest virus, and pathogenic members such as the Venezuelan, Eastern and Western equine encephalitis virus. Another pathogenic Togavirus is the rubella virus, a virus closely related to the alphaviruses and the causative agent for German measles. Coronaviruses (one of the major causative agents for common colds), and astroviruses (associated with pediatric diarrhea), are also pathogenic RNA viruses. All of these viruses are characterized by a life cycle that include the synthesis of subgenomic RNAs. For example, the Sindbis virus genome consists of a single molecule of single stranded RNA. The genomic RNA is infectious and serves as mRNA and is, by convention, of plus (+) polarity. The 5' two-thirds of the genomic RNA is translated to produce a polyprotein that is processed by co-translational and post-translational cleavage into four nonstructural proteins presumably required for RNA replication. A full-length minus (−) strand complementary to the genomic RNA is then synthesized. This minus strand serves as a template for the synthesis of a new genomic RNA plus (+) strand molecule and as a template for transcription of a subgenomic mRNA molecule. Transcription from the minus (−) strand begins at an internal site to produce the subgenomic mRNA. This internal site is referred to as the junction region or subgenomic RNA promoter region. This region of the Sindbis virus is described in U.S. Pat. No. 5,217,879 issued on Jun. 8, 1993 and is commonly assigned to the assignee of this application. The entirety of U.S. Pat. No. 5,217,879 is herein incorporated by reference hereto. Translation of the subgenomic mRNA molecule produces the structural proteins necessary for capsid and envelope formation.

Other RNA viruses which have a plus (+) strand genomic RNA, such as the flaviviruses and picornaviruses, do not synthesize subgenomic RNAs during their life cycle. Rather, these RNA viruses contain a single open reading frame for translation and the viral proteins are produced by co- and post-translational cleavage of a polyprotein. Flaviviruses are a genus of the Togaviridae family of viruses and include such pathogenic species as St. Louis encephalitis, Japanese B encephalitis, Murray Valley encephalitis, West Nile, Dengue, and Yellow Fever. The Picornaviruses include the Poliovirus, Coxsackievirus, Echovirus, Enterovirus and Rhinovirus. The clinical detection of each of these viruses is also important for the diagnosis of disease and for research purposes.

Heretofore, the detection of RNA viruses in a specimen has not included the use of indicator cell lines capable of detecting RNA viruses that replicate through an RNA intermediate and only more costly and laborious techniques have been utilized. It would be desirable, therefore, to provide a means for detecting the presence of an RNA virus in a specimen that utilizes a genetically engineered cell line so as to provide a rapid, sensitive and quantifiable in vitro assay for RNA viruses.

SUMMARY OF THE INVENTION

This invention encompasses novel compositions and methods which permit the detection of an RNA virus in a specimen. In one embodiment, a mammalian cell stably transformed with a DNA molecule which permits its use in detecting RNA viruses is provided. The DNA molecule transfected into the cell contains, in a cDNA form, the cis-acting sequences of the RNA virus genome that renders it capable of replication and transcription if the transacting enzymes from an active virus are present, and the structural coding sequence of a reporter gene product which will permit the detection of the presence of an RNA virus when the reporter gene is properly translated. In this embodiment, the reporter gene coding sequence is placed immediately downstream of the viral subgenomic RNA promoter region which is present in the RNA virus genome and included in the cDNA region. The cDNA also includes a promoter that is recognized by the DNA dependent RNA polymerase of a mammalian cell directly upstream of the 5' cis-acting sequences of the defective viral cDNA. Cells stably transformed with this DNA molecule will transcribe an RNA molecule of (+) polarity, but little or no reporter gene product will be translated in the absence of active virus. When the cell is infected with a related virus that recognizes the cis-acting sequences in the defective RNA viral genome on the (+) RNA molecule, the trans-acting elements (enzymes) synthesized by the virus will cause the replication of the (+) RNA strand into a (−) RNA strand which is then transcribed into a (+) strand subgenomic RNA molecule which serves as mRNA for the reporter gene and thus the reporter gene mRNA is translated into the reporter gene product. The presence and level of this reporter gene product thus indicates that the cell has been infected with an RNA virus.

In an alternate embodiment, a mammalian cell line is stably transformed with a DNA molecule which contains a promoter that is recognized by the DNA dependent RNA polymerase of a mammalian cell and that causes low levels of expression of a (+) polarity RNA molecule which contains the 5' cis-acting sequences derived from a defective RNA virus genome and the open reading frame of a reporter gene. Translation of this RNA will yield low levels of a polyprotein which will include the amino acid sequences of the reporter gene product, but which will be enzymatically inactive. Infection of this cell line with an RNA virus whose non-structural proteins recognize the 5' cis-acting sequences on the (+) polarity RNA molecule will result in replication of the (+) polarity RNA molecule through a (−) polarity RNA molecule intermediate and result in high levels of the (+) polarity RNA. This (+) polarity RNA will then be translated into high levels of a polyprotein which will then be specifically cleaved by the viral encoded proteases of the RNA virus. One of the products of this cleavage reaction will be the reporter gene product which will now be enzymatically active.

In another embodiment, a cell line is prepared that contains a stably transformed DNA molecule that contains a promoter that causes low levels of expression of downstream sequences in a mammalian cell and a region of cDNA derived from a structurally defective RNA viral genome that does not include a subgenomic RNA promoter region and a reporter gene placed within the structurally defective RNA viral genome. Cells stably transformed with this DNA molecule will transcribe an RNA molecule of (+) polarity but at such low levels that little or no reporter gene product will be expressed in the cell. When the cell is infected with a related virus that synthesizes the trans-acting enzymes that recognize the cis-acting sequences in the defective (+) RNA viral genome, the trans-acting enzymes will cause significant replication of the (+) RNA strand through a (−) RNA intermediate such that translation of the reporter gene product will be at a high enough level to be detected in the cell. Only one molecule of the defective viral RNA need be present in the cytoplasm of the cell for it to be recognized and amplified by the trans-acting viral enzymes. The RNA can then be translated at levels which permit detection of the reporter gene.

In a further embodiment, a method for the detection of an RNA virus in a specimen using a cell line as described above is provided. The cells are incubated with a specimen suspected of containing an RNA virus for a period of time sufficient to permit the RNA virus to replicate and synthesize its trans-acting enzymes, and the expression of the reporter gene product is detected by a suitable assay procedure. The expression of the reporter gene product, or an increased level of expression of the reporter gene product over a baseline level of expression, indicates the presence of an RNA virus in the specimen. The amount of virus in the specimen may also be quantified by this method.

In a still further embodiment, the invention provides a kit containing the reagents and supplies necessary for conducting assays for detecting RNA virus in a specimen in accordance with the method of this invention. The kit includes sufficient amounts of a supply of stably transformed cells suitably engineered to permit the detection of the RNA virus being assayed for and the reagents necessary to detect the expression of the reporter gene product.

Among the several advantages of the present invention may be noted the provision of a rapid, sensitive assay capable of detecting the presence of an infectious RNA virus in a specimen that does not rely upon the detection of viral antigens or viral nucleic acid; the provision of such an assay that utilizes stably transformed mammalian cells that only express a reporter gene product at levels high enough to be detected when the cells are infected with an RNA virus; the provision of such a method that is applicable to a variety of RNA viruses including those that synthesize subgenomic RNAs and those that contain a single open reading frame for translation; the provision of such a method that is adaptable for automated assays; and the provision of a cell line that could also be used to screen RNA antiviral agents.

DETAILED DESCRIPTION OF THE INVENTION

In accordance with the present invention, a method for detecting RNA viruses in a specimen and a stably transformed cell line for use in such method are provided. In the context of this disclosure, the following terms shall be defined as follows unless otherwise indicated:

"heterologous coding sequence" means a nucleic acid sequence which is not naturally found in association with the nucleic acid sequences of the specified molecule, cell, virus, or organism. Typically, a heterologous coding sequence encodes a non-viral RNA sequence, molecule or protein.

"RNA virus" means a virus with an RNA molecule or molecules as its genome and which replicates through an RNA intermediate.

"heterologous protein or peptide" means a protein, peptide and/or amino acid sequence not naturally encoded in a mammalian cell.

"infectious" when used to describe a virus or an RNA molecule, means a virus or RNA molecule that is self-replicating and provides for transcription in a host cell.

"RNA virus junction region" or "subgenomic promoter region" is a nucleotide sequence specific to an RNA virus that directs the transcription of an RNA molecule to produce a subgenomic mRNA molecule in the host cell.

"transfection" or "transformation" are understood to include any means for introducing an exogenous nucleic acid molecule into a host cell, including, but not limited to, adsorption, microinjection, electroporation, lipofection and the like.

"transfected" or "transformed" when used to describe a cell means a cell containing an exogenously introduced nucleic acid molecule and/or a cell whose genetic composition has been altered by the introduction of an exogenous nucleic acid molecule.

"stably transformed" when used to describe a cell means a cell containing an exogenously introduced nucleic acid molecule whereby the nucleic acid molecule is present in the nucleus of the cell and may be stably integrated into the chromosomal DNA of the host cell.

"active virus" means an RNA virus that is capable of producing the proteins necessary for replication and transcription and does replicate and transcribe.

"cis-acting sequences" means the nucleotide sequences that are necessary for the recognition of the RNA by specific proteins ("trans-acting elements") which are then able to act upon the RNA. The "trans-acting elements" are enzymes of the virus that can synthesize more RNA by replication or transcription.

"structurally defective RNA virus genome" means a nucleic acid sequence of an RNA virus that has been engineered by deletions and/or modifications of the viral genomic RNA to retain the cis-acting sequences essential for replication and transcription including any subgenomic promoter region or Junction region, but lacking one or more of the following: (1) functional non-structural genes that are responsible for the replication and transcription of the virus (the trans-acting elements), and (2) the structural proteins essential for capsid production or assembly and packaging.

"promoter" means a sequence of nucleotides which serve as a regulatory region capable of being recognized by a polymerase to initiate transcription of downstream sequences.

"replicon" means a virus or virus particle that contains the genetic information for replication, but not for assembly of the virus.

"Defective-Interfering" or "DI" means a nucleotide sequence of a virus that contains sequence information essential for their replication and packaging, but need not contain any coding information.

It has been discovered that a mammalian cell stably transformed with a cDNA copy of a structurally defective RNA virus genome into which a heterologous structural coding sequence encoding a reporter gene product such as luciferase has been introduced, and where the cDNA region is under the control of a promoter that is capable of being recognized by the DNA dependent RNA polymerase of a mammalian cell to cause the transcription of an untranslatable RNA in a mammalian cell, is capable of functioning as an indicator cell line for the detection of RNA virus in a specimen incubated with the cells. These cell lines advantageously utilize an RNA molecule constitutively transcribed in the cell as the substrate for replication and transcription from an incoming virus to permit the translation of a reporter gene product to detect the presence of the virus. When a stably transformed cell line is prepared in accordance with this invention, the reporter gene is expressed only when the non-structural proteins of the RNA virus, the trans-acting enzymes, are synthesized in the cells by an exogenously introduced, appropriately related RNA virus that expresses the trans-acting enzymes necessary to transcribe a translatable RNA from an RNA template in the cell. Because the cDNA copy of the structurally defective RNA viral genome does not synthesize functionally active mRNA at high enough levels to detect the translated protein product, the reporter gene product will only be detected if active virus is present in the specimen being analyzed.

To produce the cell lines of this invention, structurally defective RNA viral genomes of an RNA virus must first be obtained. RNA virus genomes have been engineered in a variety of ways to obtain structurally defective RNA genomes. Deletions and/or modifications of the viral RNA genome can be obtained once cDNAs have been made and then using standard molecular biological nucleic acid mutation techniques, mutant or variant viruses may be obtained. The effect of any mutation (deletion, inversion, modification, or the like) is tested by transfecting the modified RNA into cultured cells and determining if the "defective" RNA is capable of replication or transcription. If the mutation introduced into the virus renders the virus still capable of replication and transcription, it is not considered "structurally defective." Only those mutations that are incapable of replication and transcription of the viral genome are kept. Next, those defective RNAs that are replication and transcription defective are again transfected into cultured cells which are infected with active RNA virus to provide the non-structural proteins for replication and transcription in the cell. If the cis-acting sequences necessary for replication and transcription remain on the "defective" RNA viral genome, then these viruses will be replicated and transcribed in the presence of active virus and can be used in connection with the present invention. By following this procedure, a structurally defective RNA viral genome from any RNA virus that exists as a positive (+) strand genomic RNA can be obtained. A procedure by which the necessary cis-acting sequences of a virus can be determined is described in Levis, R. et. al., (1986) Cell, Vol. 44, 137–145, the entirety of which is herein incorporated by reference hereto.

Once a suitable structurally defective RNA viral genome from a selected RNA virus is obtained, a cDNA copy of the structurally defective RNA sequence is placed downstream of a promoter that is recognized by a DNA dependent RNA polymerase of a mammalian cell and capable of causing the transcription of the cDNA into RNA. This can be accomplished using standard techniques known in the molecular biological art. If necessary, linker DNA sequences are added to facilitate the ligation of the promoter to the cDNA. The promoter must be placed upstream from the viral cDNA sequence so that transcription is initiated correctly at the start of the 5' terminus of the RNA. The promoter is chosen from any promoter that is capable of causing transcription in a eukaryotic system. Exemplary promoters include the Rous sarcoma virus promoter, the SV40 viral promoter, other retroviral LTR promoters, and other suitable eukaryotic promoters known to those skilled in the art. It is preferred that the promoter be capable of transcribing only low levels of mRNA in the cell.

A heterologous structural coding sequence functioning as a reporter gene is also introduced into the cDNA copy of the structurally defective RNA viral genome. Preferably, the reporter gene is inserted in place of one or more of the viral structural proteins, but the reporter gene can be introduced as an addition to the cDNA. In RNA viruses that synthesize a subgenomic RNA, the reporter gene is introduced downstream of and under the regulatory control of the subgenomic RNA promoter or junction region so that the reporter gene is translated only in the presence of a related virus that supplies the necessary trans-acting elements to cause transcription of the subgenomic RNA containing the reporter gene. In RNA viruses that consist of a single (+) strand of virion RNA and do not synthesize subgenomic RNAs, the reporter gene is inserted into the virion RNA such that it does not affect the transcription of the RNA. Typically, in single strand RNA viruses that do not synthesize subgenomic RNAs, a single polyprotein is translated from the (+) RNA strand and subsequently cleaved to produce the viral proteins. The cDNA of a structurally defective RNA viral genome of such an RNA virus will contain the cis-acting sequences necessary for replication and the reporter gene within the structurally defective genome.

A suitable reporter gene is one that codes for an enzyme which serves as the means for detecting the presence of the RNA virus in a specimen. The enzyme is preferably one that can easily be assayed for or detected in a cell. Enzymes which are considered equally useful as the reporter gene in the cell lines of this invention generally include hydrolases or oxidoreductases and, in particular, such enzymes as β-galactosidase, β-glucosidase, β-glucuronidase, β-hexosaminidase, luciferase, phospholipase, and phosphatase.

The use of a gene encoding β-galactosidase or luciferase are particularly preferred reporter genes for use in this invention because of the numerous methods known to detect their expression and the relative sensitivity of such methods. Among these methods include histochemical assays involving a chromogenic or fluorogenic substrate which permits detection of β-galactosidase activity by a change in the color of the cell. The change in color can be detected macroscopically or microscopically. For example, methods are known which use a chromogenic substrate such as 5-bromo-4-chloro indolyl-β-D-galactopyranoside, which turns the cells blue in the presence of β-galactosidase, or a fluorogenic substrate such as fluorescein di-β-D-galactopyranoside (FDG), 3-carboxyumbelliferyl-β-D-galactopyranoside or 5-dodecanoylaminofluorescein di-β-D-galactopyranoside ($C_{12}$ FDG) which stains the cells intensely green, to detect β-galactosidase activity. Automated calorimetric assays are also available for detection of β-galactosidase activity. One such assay uses ONPG as the substrate for β-galactosidase activity in a cell lysate and the enzyme activity is detected by spectrophotometry. An automated fluorescence assay is also known. Preferably, a bacterial P-galactosidase is used, and most preferably the β-galactosidase from E. coli that is encoded by the LacZ gene.

The expression of luciferase may be detected by known luminometric methods using luciferin as the enzyme substrate. The use of luciferase as the reporter gene provides an enzymatic assay that is more sensitive than the colorimetric or fluorometric β-galactosidase assay and is also more amenable to the development of an automated assay which can detect a single infectious virus.

After the desired DNA molecule containing, in 5' to 3' orientation, a eukaryotic promoter, the cDNA of a structurally defective RNA viral genome containing a reporter gene therein and located downstream of a subgenomic RNA promoter if present, has been prepared, it is transformed into a desired cell line. Typically, the DNA molecule will be prepared on a plasmid and the plasmid will be transfected into the cell line. These procedures are well known to one of ordinary skill in the art and are described in such basic molecular biology texts as Sambrook et al., Molecular Cloning: A laboratory manual, Cold Spring Harbor, N.Y. Cold Spring Harbor Laboratory (2d ed. 1990). The cell line chosen is one that is susceptible to infection by the RNA virus being assayed for and is transformed in a manner that stably introduces the DNA molecule into the nucleus of or a chromosome of the cell. Examples of suitable susceptible cell lines for RNA viruses include baby hamster kidney cells, African green monkey cells, 3T3 mouse cells, and the like. A preferred cell line for use in preparing cell lines in accordance with the present invention are baby hamster kidney cells.

Figure 1:
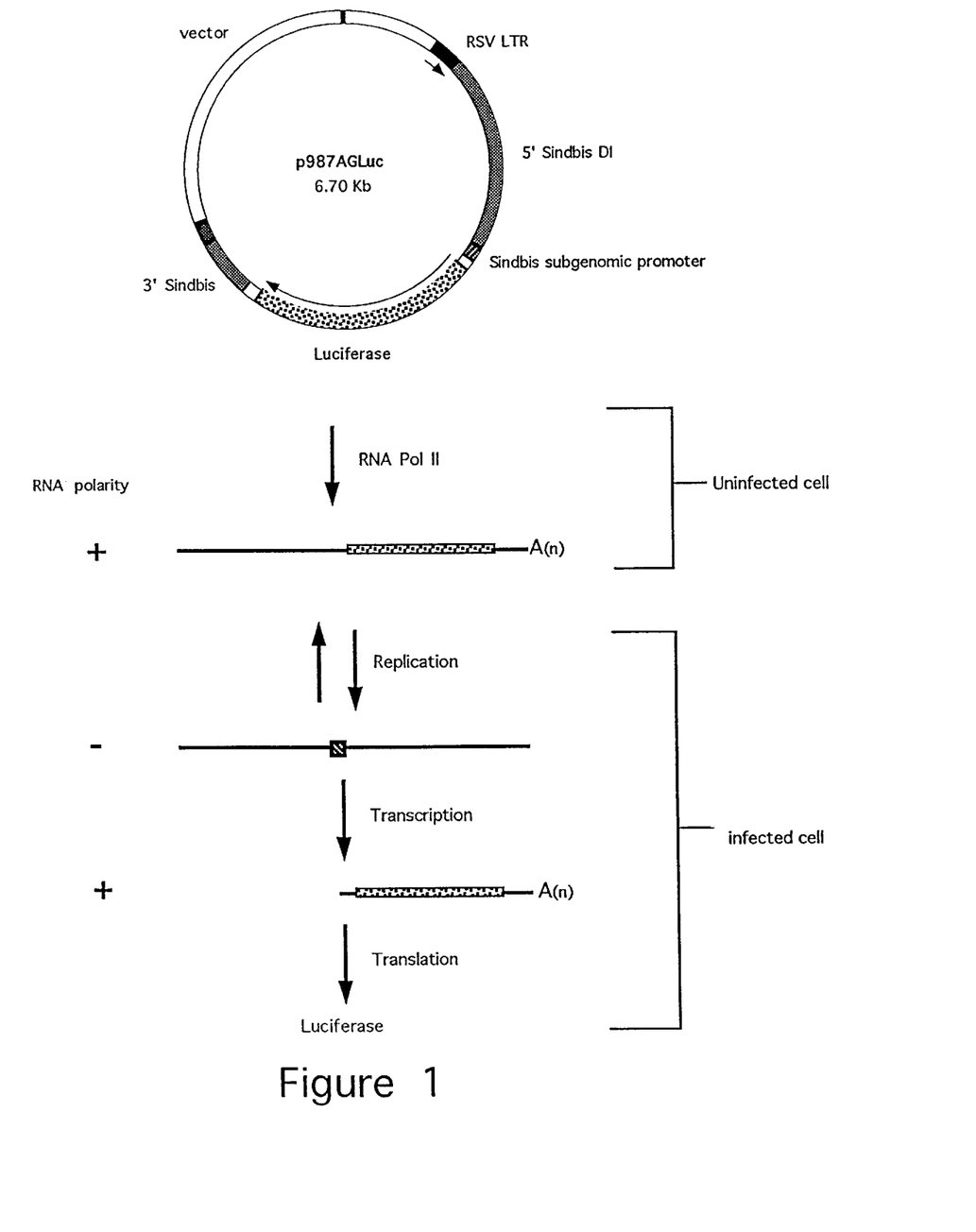
FIG. 1 is a schematic representation of the plasmid p987AGLuc used to make an exemplary cell line capable of detecting an RNA virus that includes a subgenomic intermediate in its life cycle in accordance with one embodiment of the present invention and a schematic representation of the pathways involved in generating a functional reporter gene product in accordance with one embodiment of this invention.

When a cell line is prepared in accordance with this invention, it will contain a cDNA copy of a structurally defective RNA viral genome under the control of a suitable eukaryotic promoter. The structurally defective cDNA copy of the RNA viral genome will contain the necessary cis-acting sequences, both 5' sequences and 3' sequences, essential for replication and transcription of the RNA. In one embodiment of the invention, the cell line will also contain the promoter for the subgenomic RNA with a reporter gene downstream of the subgenomic RNA promoter. This structurally defective cDNA copy of an RNA viral genome will be transcribed by the cell's DNA dependent RNA polymerase as a plus (+) strand mRNA, but no subgenomic RNA will be produced because the cell does not contain the necessary trans-acting elements (enzymes) for RNA dependent RNA replication and transcription. The subgenomic RNA requires a minus (−) strand as the template for transcription. The reporter gene located downstream of the subgenomic RNA promoter will not be translated effectively because the initiating codon will be at the 5' end of the molecule which is too far upstream of the reporter gene translational start signal. Thus, only cells that are infected with the corresponding virus or viral replicon (or a related virus) will have the transacting proteins (RNA dependent RNA polymerases) synthesized in the cell and these proteins will cause the replication of the structurally defective (+) RNA strand into the minus (−) strand and using the (−) strand as template, transcribe the subgenomic mRNA which is translated into the reporter gene product. The (−) strand also serves as a template for the (+) strand genomic RNA and the presence of the viral trans-acting enzymes will cause more (+) strand RNA and more (−) strand RNA transcripts to be synthesized. A schematic representation of a plasmid prepared in accordance with this embodiment of the invention is illustrated in FIG. 1. This exemplary plasmid configuration can be transformed into an appropriate mammalian cell line and stable transformants obtained for use as an indicator cell line to detect the RNA virus of interest. FIG. 1 also outlines the proposed mechanism by which this indicator cell line operates to detect the presence of an RNA virus in a specimen or sample. This embodiment is particularly useful for the detection of alphavirus, rubella virus, coronaviruses and astroviruses.

Figure 4:
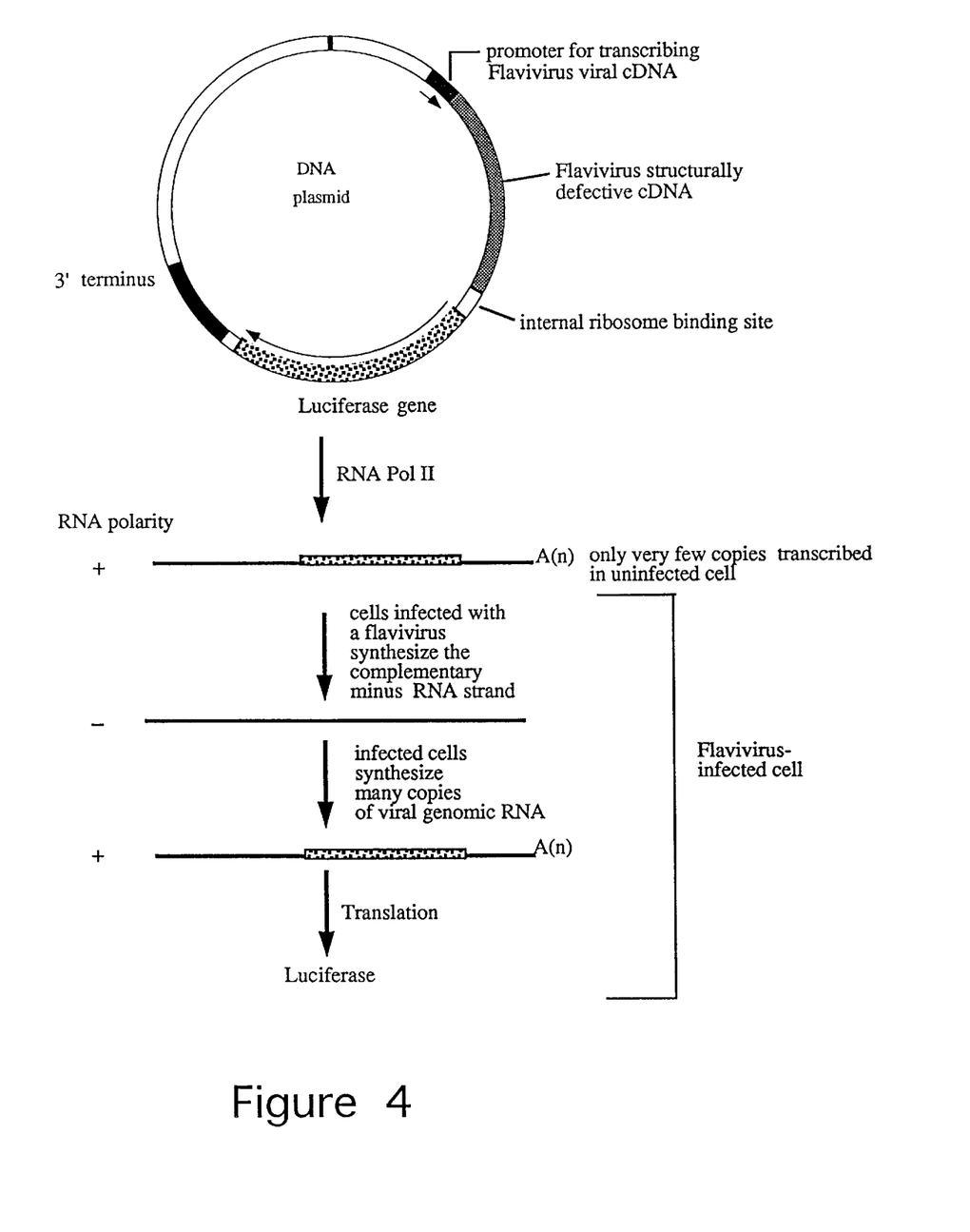
FIG. 4 is a schematic representation of a plasmid that could be used to make an exemplary cell line to detect a RNA virus that does not include a subgenomic intermediate in its life cycle and a schematic representation of the pathways involved in generating a functional reporter gene product in accordance with a second embodiment of this invention.

In an alternate embodiment, the RNA virus desired to be assayed does not have a subgenomic RNA phase in its life cycle. In this embodiment, the cell line is engineered to contain the cDNA of a structurally defective viral RNA genome as previously described except that the reporter gene is not adjacent to or operably coupled with a subgenomic promoter region. The eukaryotic promoter, such as the RSV LTR, the SV40 early promoter or like promoter, is selected to provide a very low level of transcription, as low as a single molecule of RNA, so that the level of expression of the RNA is undetectable in uninfected cells and consequently the reporter gene product is low. Cells infected with the appropriate virus will produce the enzymes able to replicate and transcribe the structurally defective RNA and the levels of mRNA will be increased resulting in detectable levels of the reporter gene product. In this embodiment, the RNA virus may provide the trans-acting enzymes for amplification of the defective RNA and/or enzymes required for proteolytic cleavage of the translation product which is required for detection of the reporter gene product activity. A schematic representation of a plasmid capable of being used in accordance with this embodiment is presented in FIG. 4. An outline of the proposed mechanism by which one would determine the presence of a flavivirus in a specimen or sample is also outlined in FIG. 4. This embodiment has particular application to flaviviruses and picornaviruses.

In order to detect the presence of an RNA virus in a specimen in accordance with the method of this invention, cells prepared in accordance with the description above are incubated with a specimen in standard culture vessels. The specimen may be any material which can be placed into a fluid or fluid environment and includes biological fluids such as blood, semen, nasopharyngeal swabs, cerebrospinal fluids and the like. The cells and the specimen are cultured for a sufficient period of time for the RNA virus infectious cycle to proceed. If the target virus is in the specimen, it will produce the nonstructural proteins necessary to cause the expression of the reporter gene which can then be measured in the cells, in the culture medium, or in cell extracts.

A kit for detecting RNA viruses in a specimen containing a supply of stably transformed mammalian cells for the detection of a selected RNA virus and the reagents necessary for the detection of the reporter gene product is prepared by placing a sufficient supply of the cells and reagents in separate containers to conduct an assay or a plurality of assays.

The method and cells of this invention are useful for the detection of RNA viruses of the Family Togaviridae including alphavirus, and rubella virus, as well as members of the flavivirus family, the coronavirus family, the astrovirus family, the picornavirus family, the calicivirus family, and viruses such as the hepatitis C virus and the hepatitis E virus. In particular, the present invention is useful in the detection of RNA viruses that synthesize a subgenomic RNA in their life cycle from a minus (−) strand of RNA as template.

The following examples of the present invention are offered by way of illustration and are not to be considered in a limiting sense.

EXAMPLE 1

This example illustrates the preparation of a mammalian cell line engineered in accordance with the teachings of this invention for the detection of the alphavirus Sindbis virus.

Baby hamster kidney cells were obtained from C. Rice (Washington University, St. Louis Mo.) and used as the mammalian cell line for preparing an exemplary cell line in accordance with this invention. These cells were transfected with a plasmid containing a Sindbis virus structurally defective cDNA that was placed under the control of a promoter that is capable of being recognized by the DNA dependent RNA polymerase of the mammalian cell. The Sindbis virus cDNA contained a structural gene encoding luciferase in place of the genes encoding the structural proteins of the Sindbis virus.

In particular, a plasmid identified as KDI25, the elements of which are described in Levis, R. et al. (1986) Cell 44, 137–145 was obtained. Briefly, the plasmid KDI25 contained the entire sequence of the cDNA of a Defective-Interfering (DI) genome of Sindbis virus and bacterial sequences containing the origin of replication, the ampicillinase gene, and the promoter region for the SP6 polymerase. As described above, a Defective-Interfering genome of a virus contains sequence information essential for their replication and packaging, but need not contain any coding information. Plasmid KDI25 was engineered using standard molecular biological techniques to contain a XhoI site at the 5' end of the DI25 sequences to obtain pDI25.3. The *Rous sarcoma* virus (RSV) promoter was selected as the promoter to cause the transcription of the structurally defective cDNA and was inserted between the BamHI and ClaI sites of the polylinker in the Bluescript vector and a SalI site was engineered at the 3' end of the RSV promoter. To position the RSV promoter upstream of the 5' terminus of the Sindbis virus defective cDNA so that the RNA transcribed from the DNA would be initiated correctly at the 5' terminus of the defective RNA, the Bluescript vector was cut with SalI and pDI25.3 was cut with XhoI to obtain the cDNA sequences of the structurally defective RNA of the Sindbis virus (the sequence being identified as DI25) and the XhoI—XhoI fragment of pDI25.3 was ligated to the SalI cut Bluescript vector to form plasmid p9-DI25.3. As a result, this plasmid has the correct sequence between the RSV promoter and the 5' terminus of the Sindbis D125 cDNA such that the 5' terminus of the Sindbis structurally defective RNA was the start site for DNA dependent RNA transcription. This plasmid was cut with ApaI, filled in, and MluI linkers inserted.

Figure 5:
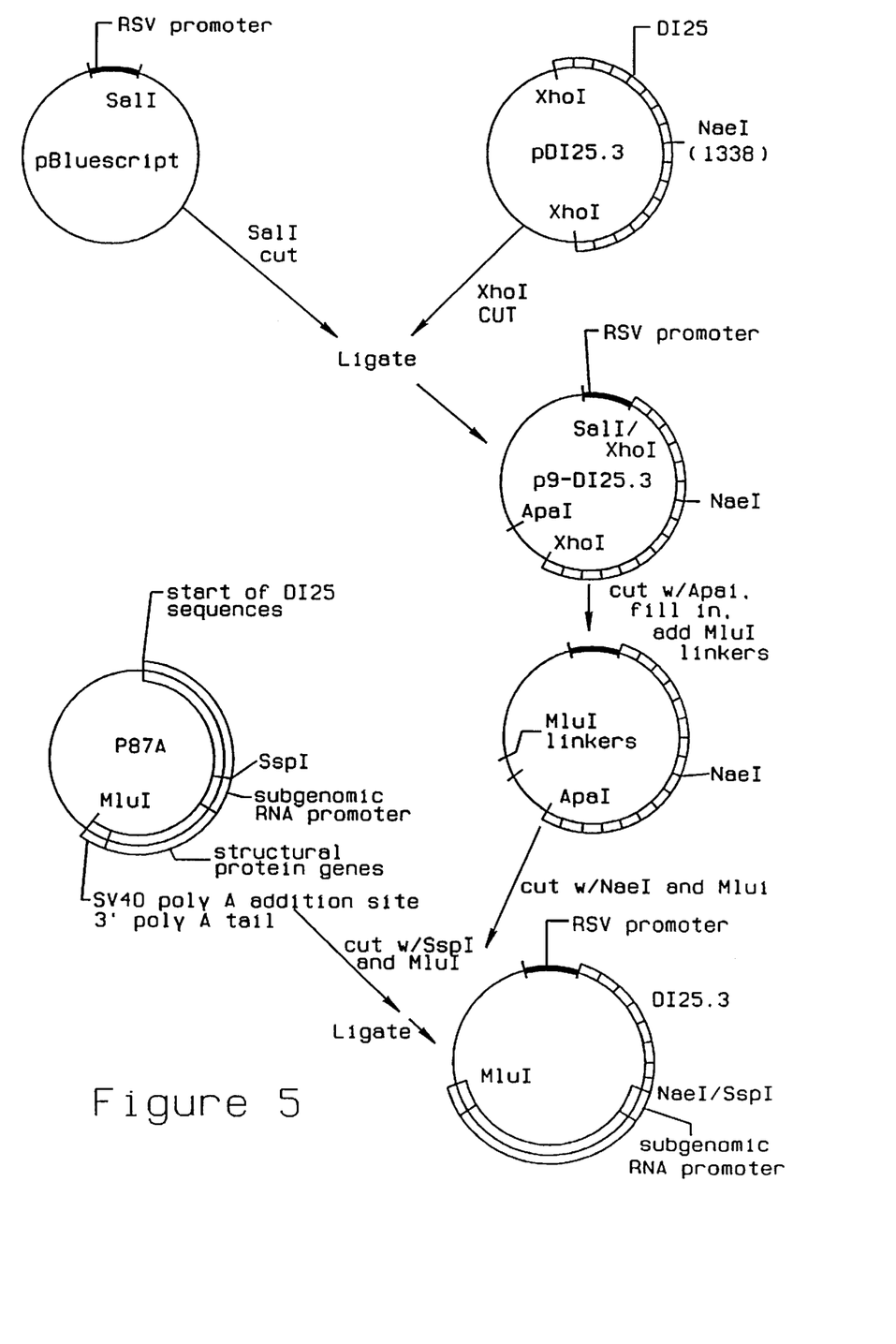
FIG. 5 is a schematic representation of the production of p987AG.

A DNA fragment containing the Sindbis virus subgenomic RNA promoter, the Sindbis structural protein genes, and a suitable 3' terminus for use as DNA in transfected cells was introduced into p9-DI25.3 by ligating a SspI-MluI DNA fragment from p87A into p9-DI25.3 that had been cut with NaeI and Mlu to remove the DNA between these sites. Plasmid p87A contained the Sindbis 5' DI25 sequences from base pair 297 to 539 followed by DNA sequences from base pair 6267 to the end of the Sindbis Toto genome as described in Rice, C. et al. (1987) J. Virol. 61:3809–3819, the entirety of which is herein incorporated by reference hereto. The DNA from the Sindbis Toto genome contains the structural protein genes and a polyA stretch. Plasmid p87A also contains an SV40 polyA addition site after the polyA stretch followed by a MluI site. The resulting plasmid is identified as p987AG. This DNA has an XbaI site 14 nucleotides downstream of the start of the subgenomic RNA and an NsiI site upstream from sequences at the 3' terminus of the viral RNA. The construction of p987AG is outlined in FIG. 5.

The structural genes between the XbaI and NsiI sites of p987AG were replaced with a structural coding sequence encoding the enzyme luciferase to function as a reporter gene in the DNA. The luciferase gene was inserted behind the Sindbis virus subgenomic promoter DNA in p987AG and was constructed in the following manner. Plasmid pT3/T7Luc (Clontech, Palo Alto Calif.) which contains the structural coding sequence for firefly luciferase was digested with SalI, blunt ended with Klenow fragment and four dNTP's and ligated to an NheI linker. pT3/T7Luc was then digested with NheI and SmaI and the resulting fragment contained the 1.9 kb luciferase gene. This gene was then cloned into the XbaI and NsiI sites of p987AG in place of the structural genes to form plasmid p987AGLuc, a schematic representation of which is shown in FIG. 1.

The BHK cells were transfected with p987AGLuc in 35 mm dishes with approximately 106 cells per dish. Five μg of linearized p987AGLuc plasmid in 50 ml of distilled water was mixed with 50 μg of lipofection mixture (Gibco, Grand Island N.Y.) and 0.5 μg of pMamNeo (Clontech, Palo Alto, Calif.) in a polystyrene tube for 15 minutes at room temperature. The cells were washed with serum free medium and the DNA/lipofection mixture was added to the cells in 4 ml serum-free medium. The cells were incubated at 37° C. for four to six hours and the medium aspirated and replaced with medium containing 10% fetal calf serum. The cells were incubated for an additional twenty-four hours and then placed in a medium containing 1 mg/ml G418 (geneticin, Gibco). The medium was changed daily for four days, at which time the vast majority of the cells were killed. The surviving cells were trypsinized and plated onto twelve 35 mm wells such that individual cells were well separated. After seven to fourteen days, colonies were picked with a trypsin/EDTA soaked sterile cotton swab and plated onto 35 mm dishes and grown to confluence in medium containing 400 μg/ml G418.

A total of twenty-one clones were analyzed. Eleven exhibited increased luciferase activity after infection with Sindbis virus. One clone, identified as BHKSINLuc2, exhibited a very high level of luciferase activity after infection with essentially no activity above baseline prior to infection. This clone was selected for further study and analysis.

EXAMPLE 2

This example illustrates the ability of a cell constructed in accordance with this invention to detect infectious Sindbis virus in a specimen.

BHKSINLuc2 cells at a concentration of $7 \times 10^4$ were plated onto 24 well tissue culture plates. The next morning the cell monolayers were either mock-infected or infected with $2 \times 10^3$ or $6 \times 10^5$ PFU of Sindbis virus. Cells were lysed in 0.2 ml of a Triton X-100 lysis buffer (50 mM Tris, pH 7.8, 1 mm DTT, 1% Triton X-100). Luciferase was assayed in luciferase reaction buffer containing 50 mM Tris-MES, pH 7.8, 10 mM magnesium acetate, 2 mM ATP, 0.3 mM luciferin (final concentrations). The assay was performed by the addition of 0.05 ml of cell lysate to 0.15 ml of two-fold concentrated reaction buffer in a 12×75 mm borosilicate test tube. This was placed into the reaction chamber of a luminometer. Immediately after closing the chamber, 0.1 ml of a luciferin solution (1 mM in water) was added and the amount of light production recorded over 13 seconds. Raw data expressed as relative light units (RLU) were recorded. Lysis buffer and BHK cell lysates routinely gave a background level of 170–200 RLU. Luciferase activity was measured at the times indicated in FIG. 2. RLU values shown in FIG. 2 are the average of three samples.

Figure 2:
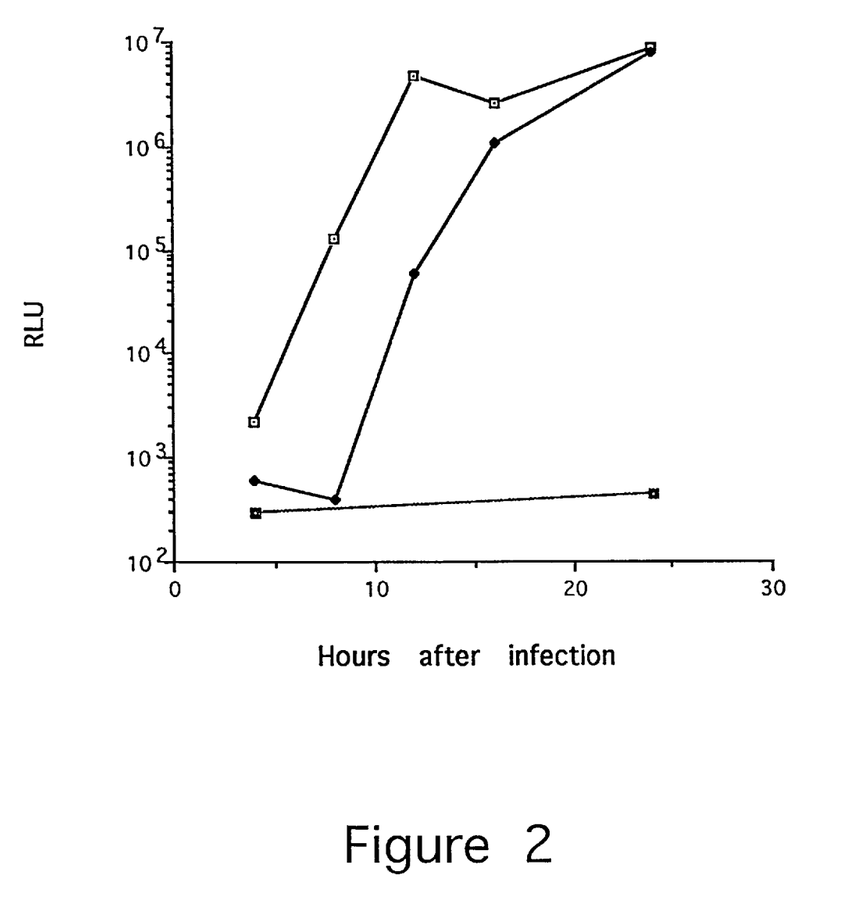
FIG. 2 is a graphical representation of luciferase activity in an exemplary cell line (BHKSINLuc2) after infection with a high or low multiplicity of infection of Sindbis virus.

As shown in FIG. 2, at higher levels of virus, luciferase activity could be detected at approximately 4 hours after infection and at the lower level of virus, luciferase activity was measurable at approximately 8–9 hours after infection. Luciferase activity at 6–8 hours post-infection was proportional to the PFU added, in the range of $10^4$ to $10^5$.

This illustrates the ability of the cell line constructed in accordance with the present invention to detect the presence of an RNA virus in a specimen.

EXAMPLE 3

This example illustrates the ability of the method of this invention to quantify the amount of RNA virus in a specimen.

Figure 3:
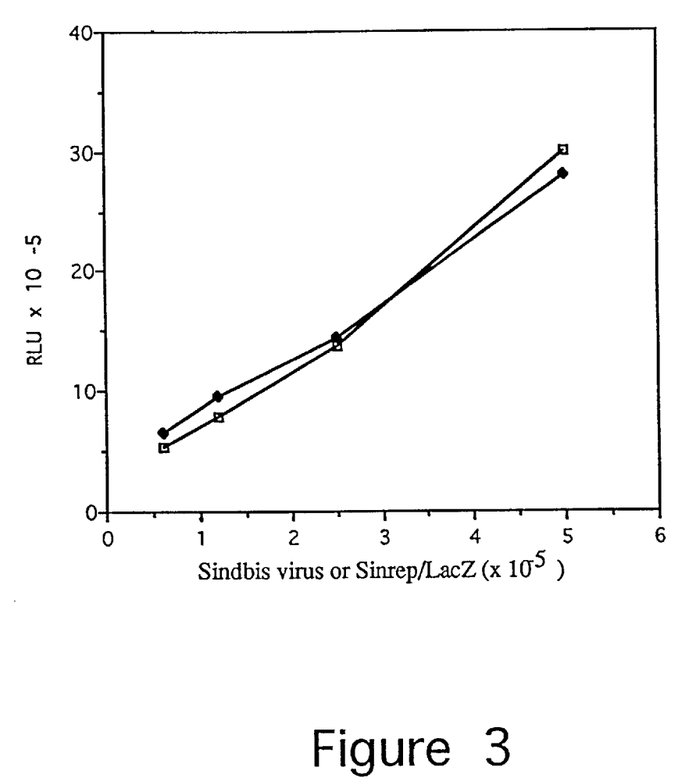
FIG. 3 is a graphical representation of luciferase activity in BHKSINLuc2 cells as a function of the concentration of Sindbis virus or Sinrep/LacZ.

In addition to assaying a Sindbis virus, a Sindbis virus replicon expressing β-galactosidase was also assayed. A titer for this replicon (Sinrep/LacZ) had previously been determined based on indirect immunofluorescence and by its ability to produce cytopathic effects. Dilutions were made so that the concentrations of Sindbis virus and Sinrep/LacZ added to the BHKSINLuc2 cells were equivalent. The infection procedure and luciferase assay were as described in Example 2 except that cells were plated in 12 well tissue culture dishes. Cell extracts were prepared 6 hours post-infection. As shown in FIG. 3, the concentration of Sindbis virus is given in PFU and that of Sinrep/LacZ in infectious units. The results illustrated in FIG. 3 that the two curves were both proportional to the input virus and virtually superimposable indicates that the luciferase assay can be used to determine the concentration of virus in an unknown sample.

EXAMPLE 4

This example illustrates the sensitivity and specificity of the method of the present invention and the cells produced in accordance therewith.

The sensitivity of the luciferase assay was compared to an assay based on the cytopathic effects (CPE) caused by infection with the Sindbis virus. BHK and BHKSINLuc2 cells were seeded, separately, into 24 well dishes at a concentration of $10^4$ cells per well. Twenty hours later, each well was inoculated with Sindbis virus at a concentration predetermined to cause CPE in about one-half of the wells. The BHKSINLuc2 cells were also assayed for luciferase activity at both 26 and 44 hours. The results are shown in Table 1.

TABLE 1

Comparison of the sensitivity of the CPE assay with the Luciferase assay for detection of Sindbis virus

| | BHKSINLuc2 Cells | | | BHK Cells |
|---|---|---|---|---|
| | Luciferase Activity | | CPE | CPE |
| PFU Added | after 26 hr | 44 hr | after 44 hr | after 44 hr |
| 15 | 16/22 | 12/22 | 12/22 | 10/20 |
| 7.5 | 4/22 | 6/22 | 5/22 | 7/20 |

The data presented in Table 1 indicate the wells that tested positive for luciferase activity over the total number of wells scored. At 26 hours, all of the samples but two had activities between $10^3$ and $10^4$ RLU above the level found in uninfected cells. For these two, one sample was 6 fold and one sample was 10 fold above background. At 44 hours, all of the positive samples had RLU greater than $10^6$. Uninfected cells had an activity of $3 \times 10^2$ RLU. The CPE was observed only at 44 hours and the numbers indicate the wells exhibiting microscopic evidence of CPE over the total number of wells scored.

These results demonstrate that the luciferase assay was equivalent to and as sensitive as the CPE assay. Furthermore, the luciferase activity could be detected in the cells after 26 hours of infection.

The BHKSINLuc2 cells were also infected with several other viruses to determine the specificity of the luciferase induction. Unrelated viruses such as influenza virus, vesicular stomatitis virus, ECHO virus, adenovirus and human cytomegalovirus did not increase the basal level of luciferase activity. In contrast, a second alphavirus, Semliki Forest virus, induced luciferase activity, but at 10-fold less than those induced by the Sindbis virus. This result was expected because structurally defective RNAs of one alphavirus will be replicated in cells infected by a related alphavirus and because the subgenomic RNA promoter of one alphavirus is recognized by other alphaviruses. Surprisingly, infection with herpes simplex virus (HSV) also led to significant increases in luciferase activity. It is likely that infection of these cells by HSV leads to an increase in the level of the defective Sindbis virus RNA which includes the luciferase open reading frame.

These results show that the cell lines of this invention may be generated to allow detection of a variety of RNA viruses.

What is claimed is:

1. A method for the detection of an active RNA virus that replicates through an RNA intermediate, the method comprising:

incubating a specimen suspected of containing said RNA virus with a mammalian cell stably transformed with a DNA molecule containing a promoter operably linked to a cDNA of a structurally defective genome of said RNA virus, wherein said cDNA contains a structural coding sequence encoding a reporter gene product, wherein said promoter is capable of causing transcription of said cDNA into an RNA molecule in a mammalian cell, and wherein the transcribed RNA molecule is replicated only in the presence of said virus; and detecting expression of said reporter gene product, wherein an increased level of expression of said reporter gene product over that in uninfected cells indicates the presence of said RNA virus in said specimen.

2. The method of claim 1 wherein said RNA virus is a flavivirus or a picornavirus.

3. The method of claim 2 wherein said reporter gene product is an enzyme capable of being detected by a colorimetric, fluorimetric, or luminometric assay.

4. The method of claim 3 wherein said enzyme is luciferase or $\mu$-galactosidase.

5. The method of claim 4 wherein the detecting step comprises assaying for the presence of luciferase or β-galactosidase.

6. The method of claim 1 wherein the specimen is a biological fluid obtained from an individual.

7. A mammalian cell for detecting the presence of an active RNA virus that replicates through an RNA intermediate, wherein said mammalian cell is stably transformed with a DNA molecule containing a promoter operably linked to a cDNA of a structurally defective genome of said RNA virus, wherein said cDNA contains a structural coding sequence encoding a reporter gene product, wherein said promoter is capable of causing transcription of said cDNA into an RNA molecule in a mammalian cell, and wherein the transcribed RNA molecule is replicated only in the presence of said virus.

8. The mammalian cell of claim 7, wherein said RNA virus is a flavivirus or a picornavirus.

9. The mammalian cell of claim 8, wherein said promoter is the *Rous sarcoma* virus LTR or an SV40 early promoter.

10. The mammalian cell of claim 7, wherein said reporter gene product is β-galactosidase or luciferase.

11. A kit for conducting assays for the presence of an active RNA virus that replicates through an RNA intermediate, said kit comprising:

a supply of mammalian cells stably transformed with a DNA molecule containing a promoter operably linked to a cDNA of a structurally defective genome of said RNA virus, wherein said cDNA contains a structural coding sequence encoding a reporter gene product, wherein said promoter is capable of causing transcription of said cDNA into an RNA molecule in a mammalian cell, and wherein the transcribed RNA molecule is replicated only in the presence of said virus; and a supply of reagents necessary to detect the expression of said reporter gene product.

12. The kit of claim 11, wherein said RNA virus is a flavivirus or a picornavirus.

13. The kit of claim 12, wherein said promoter is the *Rous sarcoma* virus LTR or or an SV40 early promoter.

14. The kit of claim 11, wherein said reporter gene product is β-galactosidase or luciferase.

* * * * *

UNITED STATES PATENT AND TRADEMARK OFFICE
CERTIFICATE OF CORRECTION

PATENT NO. : 5,851,757
DATED : December 22, 1998
INVENTOR(S) : Paul D. Olivo, Sondra Schlesinger It is certified that error appears in the above-indentified patent and that said Letters Patent is hereby corrected as shown below:

Column 14, line 2, delete "µ-galactosidase" and substitute therefor --β-galactosidase--.

Signed and Sealed this

Twelfth Day of September, 2000

Attest:

Q. TODD DICKINSON

*Attesting Officer*  *Director of Patents and Trademarks*